United States Patent [19]

Dunn, Jr. et al.

[11] Patent Number: 4,808,151

[45] Date of Patent: Feb. 28, 1989

[54] SIMPLIFIED METHOD FOR THE PREPARATION OF HUMAN LYMPHOKINE ACTIVATED KILLER CELLS

[75] Inventors: George F. Dunn, Jr., Wenonah, N.J.; Joseph D. Irr, Newark, Del.; Lise N. Halpern, Newton Highlands, Mass.

[73] Assignee: E. I. Du Pont de Nemours and Company, Wilmington, Del.

[21] Appl. No.: 42,998

[22] Filed: Apr. 27, 1987

[51] Int. Cl.$^4$ .................... A61M 37/00; A61K 37/02; A61K 45/05

[52] U.S. Cl. .......................................... 604/6; 514/2; 514/21; 530/351; 210/360.1; 210/927; 435/68

[58] Field of Search ........................ 604/4–6; 210/782, 360.1, 927; 435/41, 70, 68, 2, 240.25, 948; 424/101; 530/351, 412, 416, 417, 324, 325; 514/674, 885, 2, 21

[56] References Cited

U.S. PATENT DOCUMENTS

| | | |
|---|---|---|
| 3,145,713 | 8/1964 | Latham .................................. 604/6 |
| 4,151,844 | 5/1979 | Cullis et al. ........................... 604/6 |
| 4,185,629 | 1/1980 | Cullis et al. ........................... 604/6 |
| 4,197,847 | 4/1980 | Djerassi ................................. 604/6 |
| 4,285,464 | 8/1981 | Latham .................................. 604/6 |
| 4,401,756 | 8/1983 | Gillis ..................................... 435/68 |
| 4,416,654 | 8/1984 | Schoendorfer et al. ............... 604/6 |
| 4,464,166 | 8/1984 | Edelson ................................. 604/6 |
| 4,464,167 | 11/1983 | Schoendorfer et al. ............. 494/10 |
| 4,559,362 | 12/1985 | Umezawa et al. .................. 514/674 |
| 4,578,056 | 3/1986 | King et al. ............................ 604/6 |
| 4,613,322 | 9/1986 | Edelson ................................. 604/6 |
| 4,675,383 | 6/1987 | Bohlen et al. ....................... 530/412 |
| 4,683,889 | 8/1987 | Edelson ................................. 604/6 |
| 4,690,915 | 9/1987 | Rosenberg ............................. 514/2 |

OTHER PUBLICATIONS

Muul et al., (1987), Development of an Automated Closed System for Generation of Human Lymphokine–Activated Killer (LAK) Cells for Use in Adoptive Immunotherapy, *J. Immunol. Methods*, 101, 171–181.

Muul et al., "Large Scale Production of Human Lymphokine Activated Killer Cells for Use in Adoptive Immunotherapy", *Journal of Immunological Methods*, 88:265–275, (1986).

*Wall Street Journal*, Apr. 9, 1987, "Further Success in Using Interleukin-2 to Treat Cancer Reported by 2 Teams".

"Haemonetics Components for LAK Cell Processing", Bulletin of Haemonetics Corporation, one page.

"V50 Ficoll-Hypaque Procedure", Bulletin of Haemonetics Corporation, two pages.

*Primary Examiner*—Barry S. Richman
*Assistant Examiner*—T. J. Wallen

[57] ABSTRACT

A lymphocyte-containing white blood cell fraction obtained by standard leukapheresis, elutriation leukapheresis or standard centrifugation can be used for production of lymphokine activated killer cells by incubation with IL-2. Removal of red blood cells and granulocytes by centrifugation on ficoll is not necessary.

16 Claims, No Drawings

SIMPLIFIED METHOD FOR THE PREPARATION OF HUMAN LYMPHOKINE ACTIVATED KILLER CELLS

FIELD

This invention pertains to adoptive immunotherapy, more particularly to the in vitro generation of human lymphokine activated killer cells for use in such therapy.

BACKGROUND

Adoptive immunotherapy has recently produced encouraging clinical results against some forms of cancer. See articles in the *Wall Street Journal*, Apr. 9, 1987, and *Time Magazine*, Apr. 20, 1987. The therapy involves removing peripheral blood from a patient, removing red blood cells (RBC's) from the blood to produce a lymphocyte-containing white blood cell (WBC) fraction, incubating the blood fraction in culture medium with interleukin-2 (IL-2) to produce activated, tumor-destroying lymphocytes called LAK cells, and injecting the LAK cells and additional IL-2 into the patient. In some cases IL-2 is injected into the patient before removal of the blood in order to stimulate production of lymphocytes.

One objection to adoptive immunotherapy is that it is very expensive. One reason it is expensive is that the current procedure for producing LAK cells is labor-intensive and time consuming. This procedure is described in Muul et al., "Large scale production of human lymphokine activated killer cells for use in adoptive immunotherapy," *Journal of Immunological Methods*, 88: 265–275 (1986). As described in Muul et al., in order to generate enough LAK cells for a single treatment about $2\times10^{11}$ lymphocytes were obtained by 10 successive leukaphereses of peripheral blood. In each leukapheresis, about 10–12 liters of whole blood were processed in an automated cell separator over a 4-hour period to produce a 400–500 ml leucocyte fraction. This fraction was diluted with 2 parts of a salt solution, then poured into 50 ml conical centrifuge tubes (40 ml/tube, approx. 30–40 tubes) and underlayed with 10 ml Ficoll-Hypaque solution. The contents were centrifuged, causing separation into a platelet-rich supernatant layer, a lymphocyte-rich layer, a Ficoll-Hypaque layer, a granulocyte layer and an RBC layer. The supernatant was removed from each tube and discarded. The lymphocyte-rich fraction floating on the Ficoll-Hypaque was removed from each tube; these fractions were pooled and washed three times by suspension in salt solution and centrifugation. Since these steps must be repeated for each leukapheresis, 300–400 tubes must be handled for a single treatment.

Haemonetics Corporation of Braintree, Mass., markets an automated blood cell separator known as the Haemonetics V-50, which utilizes a 2-port conically-shaped centrifuge bowl similar to the bowl described in U.S. Pat. No. 3,145,713. The V-50 can be operated according to a standard leukapheresis protocol or according to a Surge® lymphocytopheresis protocol. The latter procedure, as described in U.S. Pat. Nos. 4,464,167 and 4,416,654, involves intermittent elutriation with previously-separated plasma, and is capable of providing more precise fractions of platelets, WBC's and RBC's than can be achieved with standard leukapheresis; it is referred to hereinafter elutriation leukapheresis.

For LAK cell processing, Haemonetics recommends use of the V-50 to separate a Buffy coat composed mostly of platelets and WBC's, followed by a secondary separation using Ficoll-Hypaque to provide a density gradient in the same centrifuge bowl for isolation of mononuclear cells (lymphocytes and monocytes) from the Buffy coat. Although this procedure is much less time-consuming and labor-intensive than the standard ficoll centrifugation described in Muul et al., it would be desirable to eliminate the ficoll separation step because it adds to the cost and can cause a reduced yield of lymphocytes. However, up to now it has been considered essential by those skilled in the art to conduct a ficoll separation in order to obtain a lymphocyte fraction sufficiently free of RBC's and granulocytes to be useful for production of LAK cells. It was assumed that RBC's and granulocytes would unduly interfere with the activation of the lymphocytes.

SUMMARY OF THE INVENTION

We have discovered that the step of ficoll density gradient centrifugation can be eliminated without unduly interfering with lymphocyte activation. Thus, our invention is an improvement in the method of producing LAK cells in vitro which comprises removing RBC's from whoe blood to produce a lymphocyte-containing WBC-rich fraction and incubating the WBC-rich fraction in culture medium with IL-2 to activate the lymphocytes. The improvement comprises using the lymphocyte-containing WBC-rich fraction without intermediate separation of a lymphocyte and monocyte layer on a ficoll gradient.

DESCRIPTION OF THE PREFERRED EMBODIMENTS

In the improved method for this invention, the RBC's can be removed in various ways. These include standard leukapheresis, elutriation leukapheresis, and centrifugation without use of ficoll. Ficoll is a synthetic water-soluble polysaccharide that has a weight average molecular weight of about 400,000 and that is widely used for the preparation of density gradients. It is available as such and in admixture with other substances under registered trademarks such as Ficoll-Paque, Ficoll-Hypaque and Ficoll-Isopaque. Leukapheresis refers to a process in which peripheral blood is withdrawn from a patient or donor, a WBC-rich fraction is separated out, and other blood fractions (plasma, platelets and RBC's) are returned to the source. Standard centrifugation is used to separate blood from donors into plasma, WBC-rich and RBC fractions which are stored for later use. (The term "Buffy coat" as used hereinafter refers specifically to the WBC-rich fraction obtained by standard centrifugation, although the term is also used in the art to refer to a platelet-rich, WBC-rich fraction obtained by leukapheresis.)

The various methods of removing RBC's produce WBC-rich fractions with varying amounts of residual RBC's and varying differentials. (The term "differential" or "diff" refers to the number percent of lymphocytes, monocytes and granulocytes based on the total number of those three cell types in a WBC-rich fraction.) Compositions of the various fractions will also vary depending upon the source. For example, a patient who has been primed with IL-2 may have a very high lymphocyte count. Typical ranges for the WBC-rich fractions obtained by various methods are compared with typical ranges for whole blood in the following table.

|  | No RBC | No WBC | Differential L | M | G |
|---|---|---|---|---|---|
| Standard Leukapheresis per 240 ml pack Vol. % RBC 10-20 | $10^{11}$ to $5 \times 10^{11}$ | $2 \times 10^9$ to $10^{11}$ | 60-80 | 5-25 | 5-25 |
| Elutriation Leukapheresis per 400 ml pack Vol. % RBC 1-6 | $2 \times 10^{10}$ to $10^{11}$ | $2 \times 10^9$ to $10^{11}$ | 80-85 | 10-20 | 1-5 |
| Buffy Coat per 40 ml pack Vol. % RBC 40-50 | $10^{11}$ to $3 \times 10^{11}$ | $10^8$ to $2 \times 10^{10}$ | 20-50 | 10-30 | 20-50 |
| Normal Whole Blood per 450 ml unit | $1.6$-$2.4 \times 10^{12}$ | $2.3$-$4.6 \times 10^9$ | 25-40 | 4-10 | 50-65 |

From the above table, it can be seen that lymphocyte-containing WBC-rich fractions usable in this invention can have RBC/WBC ratios from about 0.2 to about 300 and granulocyte contents from about 1% to about 50%. As a practical matter Buffy coats would principally be used for screening to determine whether a patient is capable of developing LAK cells. For generating LAK cells for use in adoptive immunotherapy the leukapheresis products having RBC vol. % of about 1-20% and RBC/WBC ratio of about 0.2-250 would be preferred.

At the present time, it is preferred to use the elutriation leukapheresis product because it is more nearly like the ficoll-separated products in both RBC and granulocyte content, and therefore would probably be more readily accepted by workers in the art. In addition, it appears that elutriation leukaphersis products can be cultured at a somewhat higher cell density (e.g., $1 \times 10^7$/ml or higher) than can standard leukapheresis products on a routine basis. From the above table, it can be seen that elutriation leukaphersis products typically have a RBC/WBC ratio of about 0.2 to about 50, a RBC vol. percent of about 1-6 and a granulocyte content of 1-5. More typical ranges are RBC/WBC of about 0.5-25 and RBC vol. % of about 2-4.

Standard leukapheresis can be performed using instruments available from various manufacturers, including Haemonetics, Fenwall, and Cobe and following the manufacturers' instructions. The only instrument now available for performing elutriation leukapheresis is the Haemonetics V-50. Following the teaching of U.S. Pat. Nos. 4,464,167 and 4,416,654 or the instructions provided by Haemonetics, the V-50 can be used to provide a WBC-rich fraction having low RBC and granulocyte content.

Monocyte content of the WBC-rich fraction can be reduced below the figures shown in the table by treatment of the leukapheresis product with an L-amino acid lower alkyl ester or hydrogen chloride salt thereof, e.g., methyl, ethyl, propyl, isopropyl, butyl, isobutyl or t-butyl ester of phenylamaine, glutamic acid, glutamine or tyrosine. Phenyl alanine methyl ester is preferred. Further details are given in copending U.S. application Ser. No. 868,697, filed May 30, 1986, and in the examples below.

Activation of the lymphocytes by incubation with IL-2 is accomplished in this invention in the same manner as in the prior art. Containers such as conventional flasks and roller bottles can be used, but the preferred containers are 0.2-5 liter tissue culture bags made from flexible copolymeric film materials as disclosed in copending application Ser. No. 008,273, filed Jan. 29, 1987. Most preferred is a bag made of a copolymer of 97 mol % ethylene and 1-octene. Any suitable culture medium can be used, but the preferred culture medium is RPMI 1640, which is described in "Culture of Animal Cells," Freshney, 72-73, Alan R. Liss, Inc., NY. supplemented with serum. Initial cell concentrations of up to about $1 \times 10^7$ cells/ml can be used with an elutriation leukapheresis product and up to about $1 \times 10^7$ cells/ml with a standard leukapheresis product. A concentration of at least $1 \times 10^6$ cells/ml should be used for reason of economy. Preferred ranges would be $5 \times 10^6$ to $10^7$ cells/ml for elutriation leukapheresis products and $1$-$5 \times 10^6$ cells/ml for standard leukapheresis products. The cells are incubated with IL-2 for about 2-7 days, preferably about 3-5 days, at a temperature of about 35°-39° C., preferably 37° C.

"Interleukin-2" (IL-2) as used herein means human IL-2. It includes natural and recombinant IL-2 (rIL-2) and biologically functional equivalents thereof, such as the rIL-2 muteins disclosed in U.S. Pat. No. 4,518,584. Preferably, the IL-2 is a rIL-2 composition consisting essentially of water, rIL-2 and, optionally, a polyol as described in assignee's copending application Ser. No. 825,133, filed on Jan. 31, 1986. Preferably, the IL-2 concentration in the culture medium is in the range of about $5 \times 10^2$ to about $5 \times 10^4$ pM, most preferably 1000 to 2000 pM.

The LAK cells prepared by the process of the invention can be suspended in a pharmaceutically acceptable carrier, such as saline, saline containing 5% normal human serum albumin, or Hank's balanced salt solution, to provide a composition which can be infused into a patient afflicted with a tumor. The patient is concurrently treated with rIL-2 as further described by Rosenburg et al., *The New England Journal of Medicine* 313, 1485-1492 (1985). In that modality, the patient's blood is withdrawn, subjected to leukapheresis and harvested cells are immediately cultured for 3 days to generate LAK cells. The LAK cells are then infused into the patient. Typically, about $3 \times 10^{10}$ to $14 \times 10^{10}$ LAK cells are infused in 4-9 doses. Interleukin-2 is administered every eight hours at doses such as 10,000, 30,000 or 100,000 units per kilogram of weight. The treatment consists of a two-week regime of leukapheresis and reinfusion and generally repetition starting the third week. Recombinant IL-2 can be included in the LAK cell composition.

Cytotoxicity (LAK) Assay

In the following examples, unless otherwise stated, a 4 hour $^{51}Cr$ release assay was used to measure cytotoxicity of LAK cells for tumor cells (LAK activity). Tumor cells at a concentration of about $2\times 10^6$ to $10\times 10^6$ per ml were incubated with 100 µCi of $Na_2{}^{51}CrO_4$ in 0.4 mL of Tris-phosphate buffered saline for 1 hour at 37° C. The cells were washed 3 times with RPMI 1640 containing 5% or 10% fetal calf serum (FCS) and resuspended to $10^5$ cells/mL in RMPI-20% FCS or RPMI-10% FCS. The effector cells (LAK cells) were suspended to various concentrations of 0.1 mL was added in to wells round bottom microliter plates. The $^{51}Cr$ labelled target cells (0.1 mL) were added to all wells. After 4 hours of incubation at 37° C., the plates were centrifuged and 0.1 mL of resulting supernatant was removed from each well and counted in a gamma counter. Percent cytolysis is calculated from the following formula:

$$\% \text{ cytolysis} = \frac{\text{experimental cpm} - \text{spontaneous cpm}}{\text{total cpm} - \text{spontaneous cmp}} \times 100$$

Each variable was tested in triplicate and the resulting data are expressed as % cytolysis. This cytotoxicity test is further described in "Selected Methods in Cellular Immunology," Mishell and Shiigi, eds., 124–137, W. H. Freeman and Co., San Francisco (1980).

In other experiments, the results of the assays are presented as "Lytic Units" (LU or LU30) which are the number of target cells per 100 effector cells when 30% of the target cells are killed when LAK cells and target cells are incubated together for 4 hours at 37° C. The calculation of LU is based upon the method of Pross et al., *Journal of Immunological Methods* 68, 235–249 (1984). The greater the number of LU, the greater the potency of the LAK cell preparation.

The disclosure of U.S. Pat. Nos. 4,464,167 and 4,416,654 relating to the production of a WBC-rich fraction by elutriation leukapheresis using previously separated plasma as elutriant are incorporated herein by reference.

EXAMPLE 1

Purpose (1) To study the LAK activity of cells obtained from a Haemonetics V50 using the elutriation technique to obtain white blood cells.

(2) To study the effects of phenyl alanine methyl ester (φAla) treatment and Ficoll treatment on the LAK activity of cells obtained from the Haemonetics V50 elutriation technique.

Cells

Human lymphocytes (obtained from Haemonetics Corporation using V50 elutriation technique). Raji cells.

Materials (1) Cell culture medium (CCM)=RPMI 1640 with 10% FBS, L-glutamine and Gentamicin
(2) Phosphate buffered saline (PBS) $1\times$ without $Ca^{++}$ and $Mg^{++}$
(3) Ficoll Hypaque (Ficoll)
(4) φAla
(5) Unopette ® for WBC count
(6) Ethylene butene copolymer Bag for cell culture
(7) T25 tissue culture flasks
(8) 1% NP 40
(9) $2\times TD$ buffer
(10) $^{51}Cr$ (as sodium chromate)
(11) recombinant Interleukin-2, 10 units/ml in 0.5M glucose (IL-2)
(12) 96 well µ bottom tissue culture plate
(13) SCS Harvesting System (Skatron)
(14) Beckman Gamma 4000 Counter
(15) Trypan Blue

Procedure (A) Preparation of Cells
  (1) A total of 250 ml of a white blood cell fraction was collected froma Haemonetics V50 machine using the elutriation procedure as described in U.S. Pat. Nos. 4,416,654 and 4,464,167.
  (2) A WBC count was performed using a Unopette ®. The fraction contained $1.36\times 10^7$ WBC/ml and was estimated to contain approximately 3 vol. % RBC.
  (3) The cells were then brought to a concentration of $1\times 10^7$ WBC/ml (total volume=340 ml).
  (4) 40 Ml of cells were put directly into culture (as described below).
  (5) The remaining 300 ml were treated with φAla (as described below).
(B) φAla Treatment
  (1) Place 300 ml of cells into T150 flask.
  (2) Add 30 ml of φAla to cells
  (3) Mix well (gently).
  (4) Incubate at room temperature for 40 minutes.
  (5) After incubation, separate blood into 2 aliquots each containing 165 ml
    (a) aliquot 1 was placed into culture
    (b) aliquot 2 was underlayed with Ficoll (as described below) and then placed into culture.
(C) Set Up Culture
  (1) Cells Straight from V50 (No Ficoll; No φAla)
    (a) place 40 ml cells into a 50 ml centrifuge tube
    (b) centrifuge cells 10 minutes at 1200 rpm
    (c) discard supernatant
    (d) resuspend cells in CCM to a total volume of 40 ml
    (e) place desired amount of cells into T25 flasks
    (f) add CCM to flasks to bring white cells to desired concentration
    (g) add 5 µl IL-2 to each flask (final concentration 10 units/ml)
    (h) place flasks in 37° C. incubator with 5% $CO_2$.

| | Set up 3 - T25 Flasks | |
|---|---|---|
| $1 \times 10^6$ WBC/ml | $5 \times 10^6$ WBC/ml | $1 \times 10^7$ WBC/ml |
| 1 ml cells | 5 ml cells | 10 ml cells |
| 9 ml media (CCM) | 5 ml media (CCM) | 5 µl IL-2 |
| 5 µl IL-2 | 5 µl IL-2 | |

(2) Aliquot 1→Cells from V50(φAla and No Ficoll)
    (a) place 165 ml of φAla treated cells into a 250 ml centrifuge tube
    (b) centrifuge for 10 minutes at 1200 rpm
    (c) discard supernatant
    (d) resuspend cells in 50 ml CCM (e) perform cell count using Unopette®; the WBC count was $1.9 \times 10^7$ per ml
(f) set up cultures in bags and flasks according to cell concentrations desired
(g) place cultures in 37° C. incubation with 5% $CO_2$.

Set Up 2 Cultures

T25 Flask: $5 \times 10^6$ cells/ml
Bag: $9 \times 10^6$ cells/ml $$\frac{5 \times 10^6}{1.9 \times 10^7} = .260 \times 10 = 2.6 \text{ ml cells}$$
7.4 ml media (CCM)
5 µl IL-2  } in T25 flask $$\frac{9 \times 10^6}{1.9 \times 10^7} = .474 \times 100 = 47.4 \text{ ml cells}$$
52.6 ml media (CCM)
50 µl IL-2  } in Bag (3) Aliquot 2→Cells from V50(φAla and Ficoll)
(a) place 40 ml of φAla treated cells into 4–50 ml centrifuge tubes
(b) underlay blood with 10 ml of Ficoll
(c) centrifuge for 30 minutes at 1900 rpm
(d) collect interface layer with a sterile pasteur pipette and place cells into a sterile 50 ml centrifuge tube
(e) bring volume in the tube up to 50 ml using PBS
(f) centrifuge for 10 minutes at 1200 rpm
(g) discard supernatant
(h) resuspend pellet in 50 ml of CCM
(i) centrifuge for 10 minutes at 1200 rpm
(j) resuspend in 5 ml of CCM
(k) perform cell count using trypan blue; then
(l) set up cultures in bags and flasks according to cell concentrations desired
(m) place cultures in 37° C. incubator with 5% $CO_2$.

NOTE: No interface layer resulted after step 3; therefore, the cells were resuspended, re-underlayed with Ficoll and recentrifuged. After this, the cells in the interface were collected.

Ste Up 3 Cultures

T25 Flask: $5 \times 10^6$ cells/ml
T25 Flask: $10 \times 10^6$ cells/ml
Bag: $1.9 \times 10^6$ cells/ml $$\frac{5 \times 10^6}{6.8 \times 10^7} = .074 \times 10 = .740 \text{ ml cells}$$
9.260 ml media (CCM)
5 µl IL-2  } in T25 flask $$\frac{1 \times 10^7}{6.8 \times 10^7} = .147 \times 10 = 1.47 \text{ ml cells}$$
8.53 ml media (CCM)
5 µl IL-2  } in T25 flask $$\frac{1.9 \times 10^6}{6.8 \times 10^7} = .0279 \times 100 = 2.79 \text{ ml cells}$$
97.21 ml media (CCM)
50 µl IL-2  } in T25 flask (D) LAK Assay The LAK assay was performed after cells were in culture for 4 days, according to the procedure given above.

NOTE: Due to the overabundance of red blood cells contained in the specimens, 3 specimens were treated with lysis buffer prior to the LAK assay. Lysing solution: 0.83 g Ammonium Chloride, 200 ml distilled $H_2O$
(1) resuspended cell pellet in 10 ml lysing solution
(2) incubate for 20 minutes at room temperature
(3) centrifuge for 10 minutes at 1200 rpm
(4) discard supernatant
(5) resuspende in 1 ml of CCM
(6) perform cell count
(7) set up E:T ratios as described in LAK assay procedure.

DATA
Cell Counts

| Specimen | Counts | Cells | Total Cells |
|---|---|---|---|
| Straight from V50 | 68 | $1.36 \times 10^7$ | $3.4 \times 10^9$/250 ml |
| After φAla | 97 | $1.9 \times 10^7$ | $9.7 \times 10^8$/50 ml |
| After φAla and Ficoll | 344 | $6.8 \times 10^7$ | $3.4 \times 10^8$/5 ml |

Prepare Cells for φAla Treatment  (Bring all cells to $1 \times 10^7$ cells/ml)

$$\frac{1 \times 10^7}{1.36 \times 10^7} = .735 \times 340 = 250 \text{ ml cells}$$
90 ml CCM Take off 40 ml and put into culture.
Add 30 ml of φAla to remaining cells and incubate 40 minutes at room temperature.

| Specimen | Viable | Non-Viable | % Viable | Cells/mls | Mls of Cells | Mls of Media | Total Cells |
|---|---|---|---|---|---|---|---|
| | | | Day 4 - $^{51}$Cr Release Data | | | | |
| Straight from V50 | | | | | | | |
| *$1 \times 10^6$ Flask | 39 | 3 | 92% | $7.8 \times 10^6$ | .256 | .744 | |
| *$5 \times 10^6$ Flask | 113 | 44 | 87% | $2.2 \times 10^7$ | .091 | .909 | |
| F$1 \times 10^6$ Flask | 136 | | | $2.7 \times 10^7$ | .074 | .926 | $5.4 \times 10^7$ |
| φAla No Ficoll | | | | | | | |
| *$5 \times 10^6$ Flask | 44 | 2 | 95% | $8.8 \times 10^6$ | .228 | .772 | |
| F$9 \times 10^6$ Bag | 92 | | | $1.8 \times 10^7$ | .111 | .889 | $3.6 \times 10^7$ |
| φAla and Ficoll | | | | | | | |
| $5 \times 10^6$ Flask | 154 | 21 | 88% | $3 \times 10^7$ | .067 | .933 | |
| $10 \times 10^6$ Flask | 158 | 30 | 84% | $3.2 \times 10^7$ | .063 | .937 | $6.4 \times 10^7$ |

-continued

| Specimen | Viable | Non-Viable | % Viable | Cells/mls | Mls of Cells | Mls of Media | Total Cells |
|---|---|---|---|---|---|---|---|
| $1.9 \times 10^6$ Bag | 48 | 2 | 92% | $9.6 \times 10^6$ | .208 | .792 | |
| Raji | 82 | 5 | 94% | $1.6 \times 10^7$ | .240 | 39.760 | |

Straight From V50

$1 \times 10^6$ Flask $\dfrac{2 \times 10^6}{7.8 \times 10^6} = .256$ $5 \times 10^6$ Flask $\dfrac{2 \times 10^6}{2.2 \times 10^7} = .091$ $10 \times 10^6$ Flask $\dfrac{2 \times 10^6}{2.7 \times 10^7} = .074$ φAla No Ficoll $5 \times 10^6$ Flask $\dfrac{2 \times 10^6}{8.8 \times 10^6} = .228$ $9 \times 10^6$ Bag $\dfrac{2 \times 10^6}{1.8 \times 10^7} = .111$ φAla and Ficoll $1 \times 10^6$ Flask $\dfrac{2 \times 10^6}{3 \times 10^7} = .067$ $10 \times 10^6$ Flask $\dfrac{2 \times 10^6}{3.2 \times 10^7} = .063$ $1.9 \times 10^6$ Bag $\dfrac{2 \times 10^6}{9.6 \times 10^6} = .208$ Raji $= \dfrac{1 \times 10^5}{1.6 \times 10^7} = .006 \times 40 = .240$ ml cells
39.760 ml media

| Maximum (Total) Release = | 2011 | | Spontaneous Release = | 463 | 21.0% |
|---|---|---|---|---|---|
| | 2215 | | | 469 | 21.3% |
| | 2361 | | | 573 | 26.0% |
| Avg. = | 2196 cpm | | Avg = | 502 cpm | 22.8% |

*specimens which were processed with lysing solution prior to LAK assay
F specimens counted using Unopette* method

| | Cells Straight From V50 - No φAla and No Ficoll | | | | | |
|---|---|---|---|---|---|---|
| | Flask $1 \times 10^6$ | | Flask $5 \times 10^6$ | | Flask $1 \times 10^7$ | |
| Dilution | CPM | % Cytolysis | CPM | % Cytolysis | CPM | % Cytolysis |
| 20:1 | 1011 | 30.1 | 1102 | 35.4 | 1222 | 42.5 |
| | 978 | 28.1 | 1143 | 37.9 | 1437 | 55.2 |
| | 1068 | 33.4 | 1142 | 37.8 | 1321 | 48.4 |
| | mean | 30.5 | mean | 37.0 | mean | 48.7 |
| 10:1 | 821 | 18.9 | 752 | 14.8 | 1014 | 30.2 |
| | 736 | 13.8 | 861 | 21.2 | 1072 | 33.7 |
| | 758 | 15.1 | 861 | 21.2 | 1361 | 50.7 |
| | mean | 15.9 | mean | 19.1 | mean | 38.2 |
| 5:1 | 613 | 6.6 | 757 | 15.1 | 907 | 23.9 |
| | 638 | 8.0 | 719 | 12.8 | 874 | 22.0 |
| | 591 | 5.3 | 747 | 14.5 | 815 | 18.5 |
| | mean | 6.6 | mean | 14.1 | mean | 21.5 |
| 2.5:1 | 512 | 0.6 | 635 | 7.9 | 584 | 4.9 |
| | 548 | 2.7 | 699 | 11.6 | 629 | 7.5 |
| | 495 | −0.4 | 592 | 5.3 | 1012 | 30.1 |
| | mean | 1.0 | mean | 8.3 | mean | 14.2 |

| | φAla and No Ficoll | | | |
|---|---|---|---|---|
| | Flask $5 \times 10^6$ | | Bag $9 \times 10^6$ | |
| Dilution | CPM | % Cytolysis | CPM | % Cytolysis |
| 20:1 | 838 | 19.9 | 670 | 9.9 |

-continued

| | φAla and No Ficoll | | | |
|---|---|---|---|---|
| | Flask $5 \times 10^6$ | | Bag $9 \times 10^6$ | |
| Dilution | CPM | % Cytolysis | CPM | % Cytolysis |
| | 716 | 12.7 | 962 | 27.2 |
| | 727 | 13.3 | 1158 | 38.7 |
| | mean | 15.3 | mean | 25.3 |
| 10:1 | 624 | 7.2 | 811 | 18.3 |
| | 550 | 2.9 | 723 | 13.1 |
| | 636 | 7.9 | 764 | 15.5 |
| | mean | 6.0 | mean | 15.6 |
| 5:1 | 541 | 2.3 | 719 | 12.8 |
| | 506 | 0.3 | 713 | 12.5 |
| | 654 | 9.0 | 822 | 18.9 |
| | mean | 3.9 | mean | 14.7 |
| 2.5:1 | 476 | −1.5 | 709 | 12.2 |
| | 488 | −0.8 | 713 | 12.5 |
| | 405 | −5.7 | 727 | 13.3 |
| | mean | −2.7 | mean | 12.7 |

| | φAla and No Ficoll | | | | | |
|---|---|---|---|---|---|---|
| | Flask $1 \times 10^6$ | | Flask $5 \times 10^6$ | | Flask $1 \times 10^7$ | |
| Dilution | CPM | % Cytolysis | CPM | % Cytolysis | CPM | % Cytolysis |
| 20:1 | 1030 | 31.2 | 1239 | 43.5 | 1498 | 58.8 |
| | 1010 | 30.0 | 1200 | 41.2 | 1227 | 42.8 |

-continued

| | φAla and No Ficoll | | | | | |
|---|---|---|---|---|---|---|
| | Flask 1 × $10^6$ | | Flask 5 × $10^6$ | | Flask 1 × $10^7$ | |
| Dilution | CPM | % Cyto-lysis | CPM | % Cyto-lysis | CPM | % Cyto-lysis |
| | 1069 | 33.5 | 1288 | 46.4 | 1187 | 40.5 |
| | mean | 31.6 | mean | 43.7 | mean | 47.4 |
| 10:1 | 769 | 15.8 | 982 | 28.4 | 1125 | 36.8 |
| | 781 | 16.5 | 999 | 29.4 | 1188 | 40.5 |
| | 745 | 14.4 | 939 | 25.8 | 1261 | 44.8 |
| | mean | 15.5 | mean | 27.8 | mean | 40.7 |
| 5:1 | 623 | 7.2 | 876 | 22.1 | 1127 | 36.9 |
| | 624 | 7.2 | 755 | 15.0 | 953 | 26.6 |
| | 676 | 10.3 | 759 | 15.2 | 1326 | 48.7 |
| | mean | 8.2 | mean | 17.4 | mean | 37.4 |
| 2.5:1 | 422 | −4.7 | 627 | 7.4 | 983 | 28.4 |
| | 464 | −2.2 | 556 | 3.2 | 940 | 25.9 |
| | 426 | −4.5 | 563 | 3.7 | 894 | 23.2 |
| | mean | −3.8 | mean | 4.8 | mean | 25.8 |

EXAMPLE 2

Protocol

The following diagram summarizes the protocol for this example.

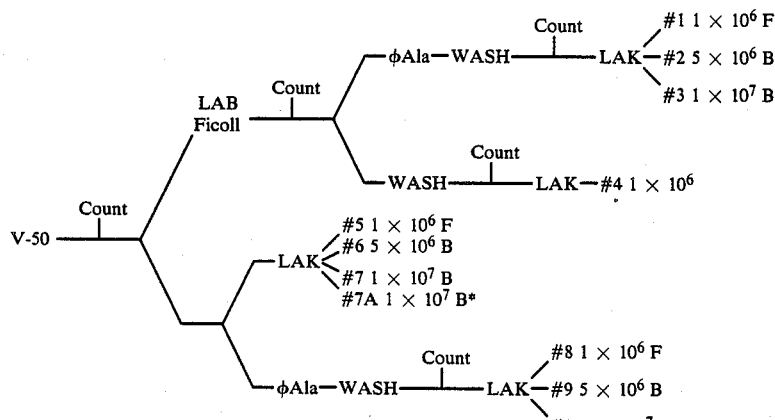

F = T-25 Flask
B = Culture Bag

Procedure (A) Separation of Cells
 (1) Cells were collected via elutriation technique on Haemonetics V-50.
 (2) A cell count was performed = $1.3 \times 10^7$ cells/ml in 442 mls. $5.8 \times 10^9$ total cells.
 (3) Cell Volume was split in two for processing.
(B) LAB Ficoll
 (1) 221 mls of cells were mixed with PBS and layered on Ficoll.
 (2) Centrifuged 30 min. at 200 rpm
 (3) Cells were then washed and counted
  256 cells viable
  99% Viability
  1 nonviable cell
  $5.1 \times 10^8$ cells ml
  $2 \times 10^9/40$ ml
 (4) Set up cells in Culture for LAK@$1 \times 10^6$

| Sample Code # | Conc. Wanted | Calculation ml cells + ml Media + μl IL-2 |
|---|---|---|
| #4 | $1 \times 10^6$ | $1 \times 10^6$ / $5.1 \times 10^7 \times 10 = 0.2$ ml + 9.8 ml + 5 μl |

(5) The remaining of these Ficoll layered cells were set up for φAla
 (a)
  $V_1C_1 = V_2C_2$
  (40 mls) $(5.1 \times 10^7) = V_2 (1 \times 10^7)$
  #mls total = $V_2$ = 200 mls
  #mls media = $V_2 - V_1$ = 160
  #mls φAla = $V_2/9$ = 200/9 = 22.2 mls φAla
 (b) Incubate 40 min and then wash.
 (c) Perform cell count and put cells in culture for LAK
  Viable cells = 229
  Nonviable = 6
  % Viability = 97%
  Cells/ml = $4.6 \times 10^7$
 (d) Set up cells for culture

| Sample Code # | Conc. Wanted | Mls Cells + Ml media + μl IL-2 |
|---|---|---|
| #1 | $1 \times 10^6$ | 0.20 ml + 9.8 mls + 5 μl |
| #2 | $5 \times 10^6$ | 10.9 mls + 89.1 ml + 50 μl |
| #3 | $1 \times 10^7$ | 21.8 ml + 78.2 ml + 50 μl |

(c) LAK directly from V-50
 (1) The second half of cells were used at this time. The amount of cells necessary to have cultures at a concentration of $1 \times 10^6$, $5 \times 10^6$ and $1 \times 10^7$ were used and the remaining cells were diluted and treated with phenyl alanine methyl ester.

| Sample Code # | Conc. Wanted | ml Cells + ml media + μl IL-2 |
|---|---|---|
| #5 | $1 \times 10^6$ | 0.76 ml + 9.2 mls + 5 μl |
| #6 | $5 \times 10^6$ | 3.9 ml + 6.1 ml + 50 μl |
| #7 | $1 \times 10^7$ | 7.7 ml + 2.3 ml + 50 μl |
| *#7A | $1 \times 10^7$ | 7.7 ml + 2.3 ml + 50 μl added |

*10 ml sample - centrifuged - removed 5 mls plasma; added 5 mls media. Diluted cells to $1 \times 10^7$.

(D) φAla without Ficoll

φAla cells without separating with Ficoll first
$C_1V_2=C_2V_2$
(200 ml) $(1.2\times 10^7)$=(k) $(1\times 10^7)$=x=260
mls media=60 mls
mls φAla=29 mls.
Incubate 40 min.
Wash.
Perform cell count and put up in culture
  Viable 240
  %Viable 93%
  Cells/ml=$4.8\times 10^7$
  Total=$1.9\times 10^9$/40 ml

| Sample Code # | Conc. Wanted | ml Cells + ml media + μl IL-2 |
|---|---|---|
| #8 | $1 \times 10^6$ | 0.2 ml + 9.8 mls + 5 μl |
| #9 | $5 \times 10^6$ | 10.4 ml + 89.6 ml + 50 μl |
| #10 | $1 \times 10^7$ | 20.8 ml + 72.2 ml + 50 μl |

All cultures were incubated for 3 days at 37° C. and 5% $CO_2$. LAK-$^{51}$Cr release performed. In the tables which follow, % REL means % Release, which is the same as % Cytolysis, calculated as explained above. E:T means the ratio of effector (LAK) cells to target (tumor) cells.
Cell counts were performed on all cultures.

| Sample | Viable | Non-Viable | % Viable | Total |
|---|---|---|---|---|
| A | 33 | 4 | 88 | $6.5 \times 10^6$/ml |
| B | 99 | 8 | 93 | $2.0 \times 10^8$/10 ml |
| C | 236 | 17 | 93 | $4.7 \times 10^8$/10 ml |
| D | 7 | 0 | 100 | $1.4 \times 10^6$/ml |
| *E | 22 | 1 | 96 | $4.4 \times 10^6$/ml |
| F | 45 | 5 | 91 | $1.8 \times 10^7$/2 ml |
| G | 38 | 4 | 90 | $7.6 \times 10^6$/ml |
| H | 75 | 6 | 93 | $1.5 \times 10^8$/10 ml |
| J | 141 | 15 | 90 | $2.8 \times 10^8$/10 ml |
| K | 31 | 4 | 89 | $6.2 \times 10^6$/ml |
| #1 | 34 | 1 | 97 | $6.8 \times 10^6$/ml |
| 2 | 162 | 8 | 95 | $3.2 \times 10^8$10/ml |
| 3 | 375 | 20 | 94 | $7.5 \times 10^8$/10 ml |
| 4 | 41 | 2 | 95 | $8.1 \times 10^6$/ml |
| 5 | 27 | 2 | 93 | $5.4 \times 10^6$/ml |
| 6 | 43 | 1 | 98 | $1.7 \times 10^7$/2 ml |
| 7 | 121 | 17 | 88 | $4.8 \times 10^7$/2 ml |
| 7A | 149 | 9 | 94 | $6.0 \times 10^7$/2 ml |
| 8 | 50 | 0 | 100 | $1 \times 10^7$/ml |
| 9 | 113 | 5 | 96 | $2.3 \times 10^8$/10 ml |
| 10 | 424 | 47 | 90 | $8.5 \times 10^8$/10 ml |

*Letter E had a heavy fibrin clot after centrifugation. Raji tumor cells were prepared as target - Viability was 100% with a concentration of $3.6 \times 10^5$/ml

| Lab Ficoll - φAla #1 @ $1 \times 10^6$ | | |
|---|---|---|
| E:T | CPM | % REL |
| 20 | 500 | 59.06 |
| 20 | 501 | 59.23 |
| 20 | 470 | 54.03 |
| 10 | 377 | 38.42 |
| 10 | 372 | 37.58 |
| 10 | 326 | 29.87 |
| 5 | 233 | 14.26 |
| 5 | 288 | 23.49 |
| 5 | 253 | 17.62 |
| 2.5 | 197 | 8.22 |
| 2.5 | 198 | 8.39 |
| 2.5 | 196 | 8.05 |

| #2 @ $5 \times 10^6$ | | |
|---|---|---|
| E:T | CPM | % REL |
| 20 | 607 | 77.01 |
| 20 | 478 | 55.37 |
| 20 | 480 | 55.70 |
| 10 | 471 | 54.19 |
| 10 | 527 | 63.59 |
| 10 | 512 | 61.07 |
| 5 | 383 | 39.43 |
| 5 | 317 | 28.36 |
| 5 | 393 | 41.11 |
| 2.5 | 338 | 31.88 |
| 2.5 | 271 | 20.64 |
| 2.5 | 242 | 15.77 |

| #3 @ $1 \times 10^7$ | | |
|---|---|---|
| E:T | CPM | % REL |
| 20 | 603 | 76.34 |
| 20 | 647 | 83.72 |
| 20 | 571 | 70.97 |
| 10 | 546 | 66.78 |
| 10 | 408 | 43.62 |
| 10 | 405 | 43.12 |
| 5 | 351 | 34.06 |
| 5 | 333 | 31.04 |
| 5 | 324 | 29.53 |
| 2.5 | 265 | 19.63 |
| 2.5 | 217 | 11.58 |
| 2.5 | 271 | 20.64 |

| STD Ficoll - No φAla #4 @ $1 \times 10^6$ | | |
|---|---|---|
| E:T | CPM | % REL |
| 20 | 565 | 69.97 |
| 20 | 507 | 60.23 |
| 20 | 529 | 62.42 |
| 10 | 483 | 56.21 |
| 10 | 400 | 42.28 |
| 10 | 462 | 52.68 |
| 5 | 276 | 21.48 |
| 5 | 255 | 17.95 |
| 5 | 291 | 23.99 |
| 2.5 | 288 | 23.49 |
| 2.5 | 263 | 19.30 |
| 2.5 | 235 | 14.60 |

| Elutriation - No Ficoll or φAla | | |
|---|---|---|
| E:T | CPM | % REL |
| #5 @ $1 \times 10^6$ | | |
| 20 | 588 | 73.83 |
| 20 | 496 | 58.39 |
| 20 | 466 | 53.36 |
| 10 | 305 | 26.34 |
| 10 | 296 | 24.83 |
| 10 | 339 | 32.05 |
| 5 | 285 | 22.99 |
| 5 | 281 | 22.32 |
| 5 | 228 | 13.42 |
| 2.5 | 211 | 10.57 |
| 2.5 | 229 | 13.59 |
| 2.5 | 237 | 14.93 |
| #6 @ $5 \times 10^6$ | | |
| 20 | 759 | 102.52 |
| 20 | 626 | 80.20 |
| 20 | 512 | 61.07 |
| 10 | 543 | 66.28 |
| 10 | 533 | 64.60 |
| 10 | 521 | 62.58 |
| 5 | 373 | 37.75 |
| 5 | 474 | 54.70 |

| Elutriation - No Ficoll or φAla | | |
|---|---|---|
| E:T | CPM | % REL |
| 5 | 408 | 43.62 |
| 2.5 | 224 | 12.75 |
| 2.5 | 341 | 32.38 |
| 2.5 | 266 | 19.80 |
| #7 @ 1 × 10$^7$ | | |
| 20 | 314 | 27.85 |
| 20 | 288 | 23.49 |
| 20 | 312 | 27.52 |
| 10 | 203 | 9.23 |
| 10 | 186 | 6.38 |
| 10 | 206 | 9.73 |
| 5 | 187 | 6.54 |
| 5 | 185 | 6.21 |
| 5 | 177 | 4.87 |
| 2.5 | 157 | 1.51 |
| 2.5 | 190 | 7.05 |
| 2.5 | 167 | 3.19 |
| #7A @ 1 × 10$^7$ | | |
| 20 | 481 | 55.87 |
| 20 | 308 | 26.85 |
| 20 | 297 | 25.00 |
| 10 | 249 | 16.95 |
| 10 | 281 | 22.32 |
| 10 | 252 | 17.45 |
| 5 | 197 | 8.22 |
| 5 | 144 | −0.67 |
| 5 | 167 | 3.19 |
| 2.5 | 160 | 2.01 |
| 2.5 | 197 | 8.22 |
| 2.5 | 164 | 2.68 |

| Elutriation - φAla, No Ficoll | | |
|---|---|---|
| E:T | CPM | % REL |
| #8 @ 1 × 10$^6$ | | |
| 20 | 592 | 74.50 |
| 20 | 574 | 71.48 |
| 20 | 463 | 52.85 |
| 10 | 377 | 38.42 |
| 10 | 438 | 48.66 |
| 10 | 425 | 46.48 |
| 5 | 257 | 18.29 |
| 5 | 228 | 13.42 |
| 5 | 431 | 47.48 |
| 2.5 | 207 | 9.90 |
| 2.5 | 217 | 11.58 |
| 2.5 | 211 | 10.57 |
| #9 @ 5 × 10$^6$ | | |
| 20 | 687 | 90.44 |
| 20 | 573 | 71.31 |
| 20 | 598 | 75.50 |
| 10 | 636 | 81.88 |
| 10 | 609 | 77.35 |
| 10 | 647 | 83.72 |
| 5 | 255 | 17.95 |
| 5 | 284 | 22.82 |
| 5 | 352 | 34.23 |
| 2.5 | 264 | 19.46 |
| 2.5 | 346 | 33.22 |
| 2.5 | 315 | 28.02 |
| #10 @ 1 × 10$^7$ | | |
| 20 | 572 | 71.14 |
| 20 | 586 | 73.49 |
| 20 | 493 | 57.89 |
| 10 | 349 | 33.72 |
| 10 | 288 | 23.49 |
| 10 | 254 | 17.79 |
| 5 | 183 | 5.87 |
| 5 | 204 | 9.40 |
| 5 | 233 | 14.26 |
| 2.5 | 205 | 9.56 |
| 2.5 | 214 | 11.07 |
| 2.5 | 195 | 7.89 |

EXAMPLE 3

A standard leukapheresis product containing 225 mls human leukocytes prepared from 3600 mls whole blood collected in 550 mls anticoagulant ACD-B was obtained from Biological Specialty Corporation, Lansdale, PA. The following procedures were performed using this product.

(1) Set up a Unopette ® (WBC) and a differential.
   Differential:
      90% Lymphocytes
      6% Monocytes
      4% Granulocytes
   Direct=165 cells
      $3.3 \times 10^7$ cells/ml
      $7.4 \times 10^9$ cells/225 mls (2) Set up cells in culture for LAK
   @$1 \times 10^6$=0.30 ml cells+9.70 ml media+5 μl IL-2
   @$5 \times 10^6$=1.52 ml cells+8.48 ml media+5 μl IL-2
   @$1 \times 10^7$=3.04 ml cells+6.96 ml media+5 μl IL-2
   Incubated @37° C., 5% CO$_2$ for 4 days.

(3) Next 20 mls of cells were removed from the remaining cells and mixed with 20 mls of PBS without Ca$^{++}$ and Mg$^{++}$. 40 mls of this mixture was layered onto 40 mls of Ficoll and centrifuged for ½ hours. Removed mononuclear cell layer and washed these cells 3 times. Performed 90 min. monocyte adherence. Washed 2 more times and performed cell count and put in culture for LAK. This is the Standard Sample.
   Standard Cell Count:
      Viable=155
      Non-viable=1
      % Viable=99%
      Cells/ml=$3.1 \times 10^7$/ml
      Total=$7.7 \times 10^8$/25 ml.
   Dilution for cell conc. of $1 \times 10^6$=0.32 ml cells+9.68 ml media+5 μl (IL-2).

(4) The remaining cells (200 mls) were then diluted with 460 mls CCM to bring the cell count to $1 \times 10^7$/ml, and treated with 72 mls φAla.
   Incubated at R.T. for 40 min.
   Cells clotted during incubation.
   Removed as much unclotted suspension as possible—washed and counted cells with WBC Unopette ®.
      26 cells viable
      1 cell nonviable
      96% viability
      $5.2 \times 10^6$ cells/ml
      $1.04 \times 10^9$ cells/200 mls.
   Put cells up in a bag at $5 \times 10^6$=48 mls cells+2 ml media+25 μl IL-2.
   Incubated at 37° C. 5% CO$_2$ for 4 days for LAK.

(5) Cell Counts After Incubation

| | Viable | Non-Viable | % Viable | Cells/ml | Total |
|---|---|---|---|---|---|
| Std. | 25 | 1 | 96 | $4.9 \times 10^6$ | — |
| Direct @ $1 \times 10^6$ | 27 | 1 | 96 | $5.3 \times 10^6$ | — |
| Direct @ $5 \times 10^6$ | 11 | 1 | 92 | $2.1 \times 10^6$ | $1.1 \times 10^7$/5 ml |
| Direct @ $1 \times 10^7$ | 24 | 5 | 83 | $4.8 \times 10^6$ | $4.8 \times 10^7$/10 ml |
| φAla @ $5 \times 10^6$ | 19 | 0 | 100 | $3.8 \times 10^6$ | |
| Raji | 85 | 7 | 92 | $1.7 \times 10^7$ | |

E:T ratio 20:1, 10:1, 5:1, 2.5:1

| Dilutions $2 \times 10^6$ | |
|---|---|
| Std. | 0.41 mls cells + 0.59 mls media |
| Direct $1 \times 10^6$ | 0.38 ml cells + 0.62 ml media |
| Direct $5 \times 10^6$ | 0.95 ml cells + 0.05 ml media |
| Direct $11 \times 10^7$ | 0.42 ml cells + 0.58 ml media |
| φAla | 0.53 ml cells + 0.47 ml media |
| Raji | 0.12 ml cells + 19.88 ml media |

Results

| E:T | Total and Spontaneous CPM Pos. Code | CPM | % Cytolysis |
|---|---|---|---|
| Blank | 1 BLAN | −5.9 | .0 |
| | 2 BLAN | −8.6 | .0 |
| | 3 BLAN | −10.3 | .0 |
| | 0 MEAN | −8.3 | .0 |
| Max. Release | 4 TOTA | 823.0 | .0 |
| | 5 TOTA | 700.9 | .0 |
| | 6 TOTA | 896.9 | .0 |
| | 0 MEAN | 806.9 | 100.0 |
| Spont. Release | 7 REFR | 104.5 | 13.0 |
| | 8 REFR | 97.5 | 12.1 |
| | 9 REFR | 109.3 | 13.5 |
| | 0 MEAN | 103.8 | .0 |
| Standard Ficoll $1 \times 10^6$ | | | |
| 20:1 | 10 UNKS | 276.5 | 24.6 |
| | 11 UNKS | 287.2 | 26.1 |
| | 12 UNKS | 309.1 | 29.2 |
| | 0 MEAN | 291.0 | 26.6 |
| 10:1 | 13 | 226.2 | 17.4 |
| | 14 | 212.4 | 15.4 |
| | 15 | 255.8 | 21.6 |
| | 0 MEAN | 231.4 | 18.2 |
| 5:1 | 16 | 174.4 | 10.0 |
| | 17 | 180.4 | 10.9 |
| | 18 | 162.4 | 8.3 |
| | 0 MEAN | 172.4 | 9.8 |
| 2.5:1 | 19 | 134.2 | 4.3 |
| | 20 | 124.8 | 3.0 |
| | 21 | 99.6 | −.6 |
| | 0 MEAN | 119.5 | 2.2 |
| Direct - No Ficoll $1 \times 10^6$ | | | |
| 20:1 | 22 | 490.6 | 55.0 |
| | 23 | 436.5 | 47.3 |
| | 24 | 423.7 | 45.5 |
| | 0 MEAN | 450.3 | 49.3 |
| 10:1 | 25 | 484.5 | 54.1 |
| | 26 | 526.7 | 60.1 |
| | 27 | 495.8 | 55.8 |
| | 0 MEAN | 502.4 | 56.7 |
| 5:1 | 28 | 391.6 | 40.9 |
| | 29 | 395.3 | 41.5 |
| | 30 | 432.2 | 46.7 |
| | 0 MEAN | 406.4 | 43.0 |
| 2.5:1 | 31 | 236.5 | 18.9 |
| | 32 | 298.4 | 27.7 |
| | 33 | 220.7 | 16.6 |
| | 0 MEAN | 251.9 | 21.1 |
| Direct - No Ficoll $5 \times 10^6$ | | | |
| 20:1 | 34 | 409.2 | 43.4 |
| | 35 | 370.9 | 38.0 |
| | 36 | 361.2 | 36.6 |
| | 0 MEAN | 380.5 | 39.3 |
| 10:1 | 37 | 352.4 | 35.4 |
| | 38 | 409.3 | 43.4 |
| | 39 | 364.4 | 37.1 |
| | 0 MEAN | 375.3 | 38.6 |
| 5:1 | 40 | 313.3 | 29.8 |
| | 41 | 293.3 | 27.0 |
| | 42 | 292.5 | 24.0 |
| | 0 MEAN | 293.1 | 26.9 |
| 2.5:1 | 43 | 194.5 | 12.9 |
| | 44 | 227.2 | 17.6 |
| | 45 | 194.9 | 13.0 |
| | 0 MEAN | 205.5 | 14.5 |
| Direct - No Ficoll $1 \times 10^7$ | | | |

-continued

| E:T | Total and Spontaneous CPM Pos. Code | CPM | % Cytolysis |
|---|---|---|---|
| 20:1 | 46 | 245.6 | 20.2 |
| | 47 | 193.2 | 12.7 |
| | 48 | 195.7 | 13.1 |
| | 0 MEAN | 211.5 | 15.3 |
| 10:1 | 49 | 191.3 | 12.4 |
| | 50 | 188.6 | 12.1 |
| | 51 | 232.2 | 18.3 |
| | 0 MEAN | 204.1 | 14.3 |
| 5:1 | 52 | 174.1 | 10.0 |
| | 53 | 166.8 | 9.0 |
| | 54 | 161.8 | 8.2 |
| | 0 MEAN | 167.6 | 9.1 |
| 2.5:1 | 55 | 136.0 | 4.6 |
| | 56 | 149.8 | 6.5 |
| | 57 | 114.9 | 1.6 |
| | 0 MEAN | 133.6 | 4.2 |
| φAla $5 \times 10^6$ | | | |
| 20:1 | 58 | 278.1 | 24.8 |
| | 59 | 221.1 | 16.7 |
| | 60 | 226.6 | 17.5 |
| | 0 MEAN | 241.9 | 19.6 |
| 10:1 | 61 | 206.5 | 14.6 |
| | 62 | 188.9 | 12.1 |
| | 63 | 195.9 | 13.1 |
| | 0 MEAN | 197.1 | 13.3 |
| 5:1 | 64 | 186.5 | 11.8 |
| | 65 | 199.8 | 13.7 |
| | 66 | 173.3 | 9.9 |
| | 0 MEAN | 186.5 | 11.8 |
| 2.5:1 | 67 | 199.2 | 13.6 |
| | 68 | 175.1 | 10.1 |
| | 69 | 212.7 | 15.5 |
| | 0 MEAN | 195.7 | 13.1 |

EXAMPLE 4

A standard leukapheresis product containing 230 mls human leukocytes prepared from 3600 ml whole blood collected in 520 mls anticoagulant ACD-B was obtained from Biological Specialty Corporation, Lansdale, PA. The following procedures were performed using this product.

(1) Removed 10 mls of cells
  (A)
  (1) Took 5 mls of this blood and mixed with 5 mls of PBS
  (2) Underlayered 10 mls of Ficoll
  (3) Centrifuged for 30 min @2000 rpm
  (4) Washed and counted
  (5) This was the Standard @$1.5 \times 10^6$ cells/ml in 10 ml flask Standard
  Viable=49
  Non-viable=0
  % Viable=100%
  Cells/ml=$9.8 \times 10^6$/ml
  Total=$1.96 \times 10^8$/20 ml.
Dilution: 1.5 ml cells+8.5 mls media+1 μl IL-2
(b)
  (1) The second 5 mls was used for direct testing
  (2) A WBC (via Unopette®) and differential were performed:
  (3) WBC $4.5 \times 10^7$/ml, $2.25 \times 10^8$/5 ml
    Diff.: 72% Lymphocytes, 22% Granulocytes, 6% Monocytes
  (4) Cells were then put up in culture at $1.5 \times 10^6$/ml and $5 \times 10^6$/ml in 10 ml flasks
    $1.5 \times 10^6$/ml=0.33 ml/cells+9.67 ml media+1 μl IL-2

$5 \times 10^6$/ml = 1.11 ml/cells + 8.89 ml media + 1 μl IL-2

Cells were incubated 4 days; chromium release assay was run.

Cell Count

|  | Viable | Non-Viable | % Viable | Cells/ml |
|---|---|---|---|---|
| Standard $1.5 \times 10^6$ | 40 | 3 | 93 | $8 \times 10^6$ |
| Direct @ $1.5 \times 10^6$ | 40 | 2 | 94 | $8 \times 10^6$ |
| Direct @ $5 \times 10^6$ | 24 | 1 | 96 | $4.8 \times 10^6$ |
| Raji | 40 | 6 | 87 | $8 \times 10^6$ |

(2) LAK Assay
E:T ratio 40:1, 20:1, 10:1, 5:1, 2.5:1 1.25:1
  Cells were diluted to $4 \times 10^6$
  Raji's were diluted to $1 \times 10^5$

| Dilutions | |
|---|---|
| Std. | 0.5 ml cells + 0.5 ml media |
| Direct $1.5 \times 10^6$ | 0.5 ml cells + 0.5 ml media |
| Direct $5 \times 10^6$ | 0.83 ml cells + 0.17 ml media |
| Raji | 0.25 ml cells + 19.75 ml media |

Results

| E:T | Total and Spontaneous CPM | | |
|---|---|---|---|
| | Pos. Code | CPM | % Cytolysis |
| Blank | 1 BLAN | −11.0 | .0 |
| | 2 BLAN | −10.6 | .0 |
| | 3 BLAN | −10.6 | .0 |
| | 0 MEAN | −10.7 | .0 |
| Max. Release | 4 TOTA | 576.9 | .0 |
| | 5 TOTA | 564.6 | .0 |
| | 6 TOTA | 584.6 | .0 |
| | 0 MEAN | 575.4 | 100.0 |
| Spont. Release | 7 REFR | 139.7 | 24.3 |
| | 8 REFR | 140.6 | 24.4 |
| | 9 REFR | 152.3 | 26.5 |
| | 0 MEAN | 144.2 | .0 |
| Standard $1.5 \times 10^6$ | | | |
| 40:1 | 10 UNKS | 540.1 | 91.8 |
| | 11 UNKS | 547.0 | 93.4 |
| | 12 UNKS | 518.3 | 86.8 |
| | 0 MEAN | 535.2 | 90.7 |
| 20:1 | 13 | 459.5 | 73.1 |
| | 14 | 503.2 | 83.3 |
| | 15 | 458.0 | 72.8 |
| | 0 MEAN | 473.6 | 76.4 |
| 10:1 | 16 | 404.5 | 60.4 |
| | 17 | 410.8 | 61.8 |
| | 18 | 439.1 | 68.4 |
| | 0 MEAN | 418.1 | 63.5 |
| 5:1 | 19 | 320.5 | 40.9 |
| | 20 | 279.1 | 31.3 |
| | 21 | 275.0 | 30.3 |
| | 0 MEAN | 291.5 | 34.2 |
| 2.5:1 | 22 | 222.1 | 18.1 |
| | 23 | 253.0 | 25.2 |
| | 24 | 232.1 | 20.4 |
| | 0 MEAN | 235.7 | 21.2 |
| 1.25:1 | 25 | 175.7 | 7.3 |
| | 26 | 205.6 | 14.2 |
| | 27 | 207.9 | 14.8 |
| | 0 MEAN | 196.4 | 12.1 |
| Direct - No Ficoll $1.5 \times 10^6$ | | | |
| 80:1 | 28 | 415.5 | 62.9 |
| | 29 | 393.0 | 57.7 |
| | 30 | 461.8 | 73.7 |
| | 0 MEAN | 423.4 | 64.8 |
| 40:1 | 31 | 417.7 | 63.4 |
| | 32 | 404.2 | 60.3 |
| | 33 | 405.6 | 60.6 |
| | 0 MEAN | 409.2 | 61.5 |
| 20:1 | 34 | 381.1 | 55.0 |
| | 35 | 407.0 | 60.9 |
| | 36 | 447.9 | 70.4 |
| | 0 MEAN | 412.0 | 62.1 |
| 10:1 | 37 | 430.5 | 66.4 |
| | 38 | 407.4 | 61.0 |
| | 39 | 442.6 | 69.2 |
| | 0 MEAN | 426.8 | 65.5 |
| 5:1 | 40 | 337.5 | 44.8 |
| | 41 | 357.4 | 49.5 |
| | 42 | 358.0 | 49.6 |
| | 0 MEAN | 351.0 | 48.0 |
| 2.5:1 | 43 | 240.8 | 22.4 |
| | 44 | 270.9 | 29.4 |
| | 45 | 262.1 | 27.3 |
| | 0 MEAN | 257.9 | 26.4 |
| 1.25:1 | 46 | 186.9 | 9.9 |
| | 47 | 194.1 | 11.6 |
| | 48 | 182.7 | 8.9 |
| | 0 MEAN | 187.9 | 10.1 |
| Direct - No Ficoll $5 \times 10^6$ | | | |
| 40:1 | 49 | 391.0 | 57.2 |
| | 50 | 392.1 | 57.5 |
| | 51 | 399.6 | 59.2 |
| | 0 MEAN | 394.2 | 58.0 |
| 20:1 | 52 | 386.3 | 56.2 |
| | 53 | 381.1 | 54.9 |
| | 54 | 377.0 | 54.0 |
| | 0 MEAN | 381.5 | 55.0 |
| 10:1 | 55 | 346.0 | 46.8 |
| | 56 | 346.0 | 46.8 |
| | 57 | 325.5 | 42.0 |
| | 0 MEAN | 339.2 | 45.2 |
| 5:1 | 58 | 296.5 | 35.3 |
| | 59 | 236.6 | 21.4 |
| | 60 | 239.0 | 22.0 |
| | 0 MEAN | 257.4 | 26.2 |
| 2.5:1 | 61 | 190.6 | 10.8 |
| | 62 | 172.8 | 6.6 |
| | 63 | 190.5 | 10.7 |
| | 0 MEAN | 184.6 | 9.4 |
| 1.25:1 | 64 | 151.7 | 1.7 |
| | 65 | 172.5 | 6.6 |
| | 66 | 203.8 | 13.8 |
| | 0 MEAN | 176.0 | 7.4 |

EXAMPLE 5

Materials

Buffy coat—52 mls of blood
  Cell count
    $4.3 \times 10^7$ cells/ml (total WBC)
    $1.8 \times 10^7$ neutrophils/ml (42%)
    (est.) $1-2 \times 10^7$ lymphocytes/ml (20-50%)
    (est.) $5 \times 10^9$ RBC/ml
    (est.) $0.5-1 \times 10^7$ monocytes/ml
Ficoll-Hypaque (Ficoll)
CCM—5% FCS—RPMI Procedures (1) No Ficoll
  (a) To 10.5 ml of Buffy coat add 215 ml CCM. Cell Count $2 \times 10^6$ cells/ml (total WBC)
  (b) Add 10 μl/ml of IL-2
  (c) Place 112 ml of culture mix in flask
  (d) Place 112 ml of culture mix in bag
  (e) Incubate at 37° C. for 20 days.
  (f) Sample at 3, 6, 12, 17 and 20 days for cell count and $^{51}$Cr Release (LAK) assay.
(2) Ficoll
  (a) Put 42 mls Buffy Coat in 50 ml centrifuge tube
  (b) Centrifuge at 800 g for 10 minutes.

(c) Discard supernatant, recover mononuclear WBC layer (Lymphocytes and monocytes) floating on Ficoll layer, wash 3×. 300×10⁶ total mononuclear cells isolated.
(d) Add CCM to provide mononuclear cell concentration of 2×10⁶/ml
(e) Place 75 ml in flask
(f) Place 75 ml in bag
(g) Incubate at 37° C. for 20 days
(h) Sample at 3, 6, 12, 17 and 20 days for cell count and $^{51}$Cr release (LAK) assay.

| Days Culture | Summary of Cell Counts (# × 10⁶/ml) | | | |
|---|---|---|---|---|
| | Flasks | | Bags | |
| | Ficoll | No Ficoll | Ficoll | No Ficoll |
| 0 | 2 × 10⁶ | 2 × 10⁶ | 2 × 10⁶ | 2 × 10⁶ |
| 3 | 1.5 × 10⁶ | 0.9 × 10⁶ | 2.1 × 10⁶ | .7 × 10⁶ |
| 6 | 2 × 10⁶ | 0.4 × 10⁶ | 2 × 10⁶ | .8 × 10⁶ |
| 12 | 2.5 × 10⁶ | 1.4 × 10⁶ | 2.7 × 10⁶ | 2 × 10⁶ |
| 17 | 1.6 × 10⁶ | 1.2 × 10⁶ | 1.9 × 10⁶ | 1.1 × 10⁶ |
| 20 | 1.1 × 10⁶ | 0.6 × 10⁶ | 2.4 × 10⁶ | 1.2 × 10⁶ |

| Days Culture | Summary of LAK Activity 3 LU$_{30}$ | | | |
|---|---|---|---|---|
| | Flasks | | Bags | |
| | Ficoll | No Ficoll | Ficoll | No Ficoll |
| 3 | 10 | 40 | 5 | 20 |
| 6 | 5 | 100 | 5 | 14 |
| 12 | 2.5 | 1 | 2 | <1 |
| 17 | 7 | <1 | 7 | 1 |
| 20 | 7 | 2 | 2.5 | 1 |

We claim:

1. In the method of producing lymphokine activated killer cells in vitro which comprises removing red blood cells and plasma from whole blood to produce a lymphocyte-containing white blood cell-rich fraction and incubating the white blood cell-rich fraction in culture medium with interleukin-2, the improvement which comprises removing red blood cells and plasma and using the white blood cell-rich fraction without an intermediate separation of lymphocytes on a ficoll gradient.

2. Method of claim 1 wherein the red blood cells are removed by leukapheresis and the volume percent of red blood cells in the white blood cell-rich fraction is in the range of about 1-20.

3. Method of claim 2 wherein the red blood cell to white blood cell ratio in the white blood cell-rich fraction is in the range of about 0.2-250.

4. Method of claim 2 wherein the white blood cell-rich fraction is washed with salt solution prior to incubation to inhibit clotting.

5. Method of claim 1 wherein the red blood cells are removed by elutriation leukapheresis and the volume percent of red blood cells in the white cell-rich fraction is in the range of about 1-6.

6. Method of claim 5 wherein the red blood cell to white blood cell ratio in the white blood cell-rich fraction is in the range of about 0.2-50.

7. Method of claim 6 wherein the white blood cell fraction has a differential of about 80-85% lymphocytes, about 10-20% monocytes, and about 1-5% granulocytes.

8. Method of claim 7 wherein the volume percent red blood cells in the white blood cell-rich fraction is in the range of about 2-4, and the red blood cell to white blood cell ratio in the white blood cell-rich fraction is in the range of about 0.5-25.

9. Method of claim 1 wherein monocytes are depleted by treatment with phenyl alanine methyl ester before incubation of the white blood cell-rich fraction.

10. In the method of generating lymphokine activated killer cells by incubating a lymphocyte-containing white blood cell-rich fraction in culture medium with interleukin-2, the improvement which comprises incubating with interleukin-2 a lymphoctye-containing white blood cell-rich fraction having a red blood cell to white blood cell ratio by number in the range of about 0.2 to 300 and a red blood cell volume percent of about 1-50.

11. Method of claim 10 wherein the red blood cell to white blood cell ratio is in the range of about 0.2-250 and the red blood cell volume percent is in the range of about 1-20 in the white blood cell-rich fraction.

12. Method of claim 11 wherein the red blood cell to white blood cell ratio is in the range of about 0.2-50 and the red blood cell volume percent is in the range of about 1-6 in the white blood cell-rich fraction.

13. Method of claim 12 wherein white blood cell-rich fraction has a differential of about 1-5% granulocytes, 0-20% monocytes and greater than about 80% lymphocytes.

14. Method of claim 13 wherein the red blood cell to white blood cell ratio is in the range of about 0.5-25 and the red blood cell volume content is about 2-4 in the white blood cell-rich fraction.

15. In the method of treatment of a cancer patient by adoptive immunotherapy which comprises removing pg,43 peripheral blood from the patient, separating a lymphocyte-containing white blood cell-rich fraction from the blood, incubating the lymphocyte-containing white blood cell-rich fraction with interleukin-2 to produce lymphokine-activated killer cells, and reinjecting the activated cells into the patient, the improvement which comprises separating the lymphocyte-containing WBC-rich fraction without use of a ficoll gradient, whereby the volume percent of red blood cells in the white blood cell-rich fraction is in the range of about 1-20.

16. Method of claim 15 wherein the lymphocyte-containing white blood cell-rich fraction is separated by elutriation leukapheresis whereby the volume percent of red blood cells in the white blood cell fraction is in the range of about 1-6.

* * * * *